United States Patent [19]

Trobridge

[11] Patent Number: 5,578,834
[45] Date of Patent: Nov. 26, 1996

[54] ELECTRICAL/OPTICAL INTERFACE COUPLER

[75] Inventor: Rex Trobridge, Costa Mesa, Calif.

[73] Assignee: Tracker Technologies, Inc., Long Beach, Calif.

[21] Appl. No.: 263,380

[22] Filed: Jun. 21, 1994

[51] Int. Cl.[6] ................................. G02B 27/00
[52] U.S. Cl. ................ 250/551; 359/143; 359/144
[58] Field of Search ................ 250/551; 359/143, 359/144, 163

[56] References Cited

U.S. PATENT DOCUMENTS

| | | |
|---|---|---|
| 4,088,981 | 5/1978 | Gott . |
| 4,214,214 | 7/1980 | Merriman . |
| 4,258,421 | 3/1981 | Juhasz et al. . |
| 4,369,361 | 1/1983 | Swartz et al. . |
| 4,530,069 | 7/1985 | Desrochers . |
| 4,603,320 | 7/1986 | Farago . |
| 4,800,512 | 1/1989 | Busch . |
| 4,829,244 | 5/1989 | Tom et al. . |
| 5,007,697 | 4/1991 | Chadha . |
| 5,099,437 | 3/1992 | Weber . |
| 5,109,454 | 4/1992 | Okuno et al. . |
| 5,157,687 | 10/1992 | Tymes . |
| 5,210,427 | 5/1993 | Uchida et al. ............... 250/551 |
| 5,233,169 | 8/1993 | Longacre, Jr. . |
| 5,258,604 | 11/1993 | Behrens et al. . |

FOREIGN PATENT DOCUMENTS

| | | |
|---|---|---|
| WO89/06075 | 6/1989 | WIPO . |

OTHER PUBLICATIONS

Brochure: Symbol Technologies, Inc. Brochure entitled "PS 1000 Series Portable Bar Code Printers".

*Primary Examiner*—Georgia Y. Epps
*Assistant Examiner*—Jacqueline M. Steady
*Attorney, Agent, or Firm*—Fulwider, Patton, Lee & Utecht, LLP

[57] ABSTRACT

A removable coupler including first and second ends, the first end connected to an electrical connector and the second end attached to an optical connector. The optical connector includes a housing containing electronics therein to convert electrical signals to signals which are transmitted optically. The housing may also or alternatively include electronics therein to convert signals received optically to electrical signals.

24 Claims, 4 Drawing Sheets

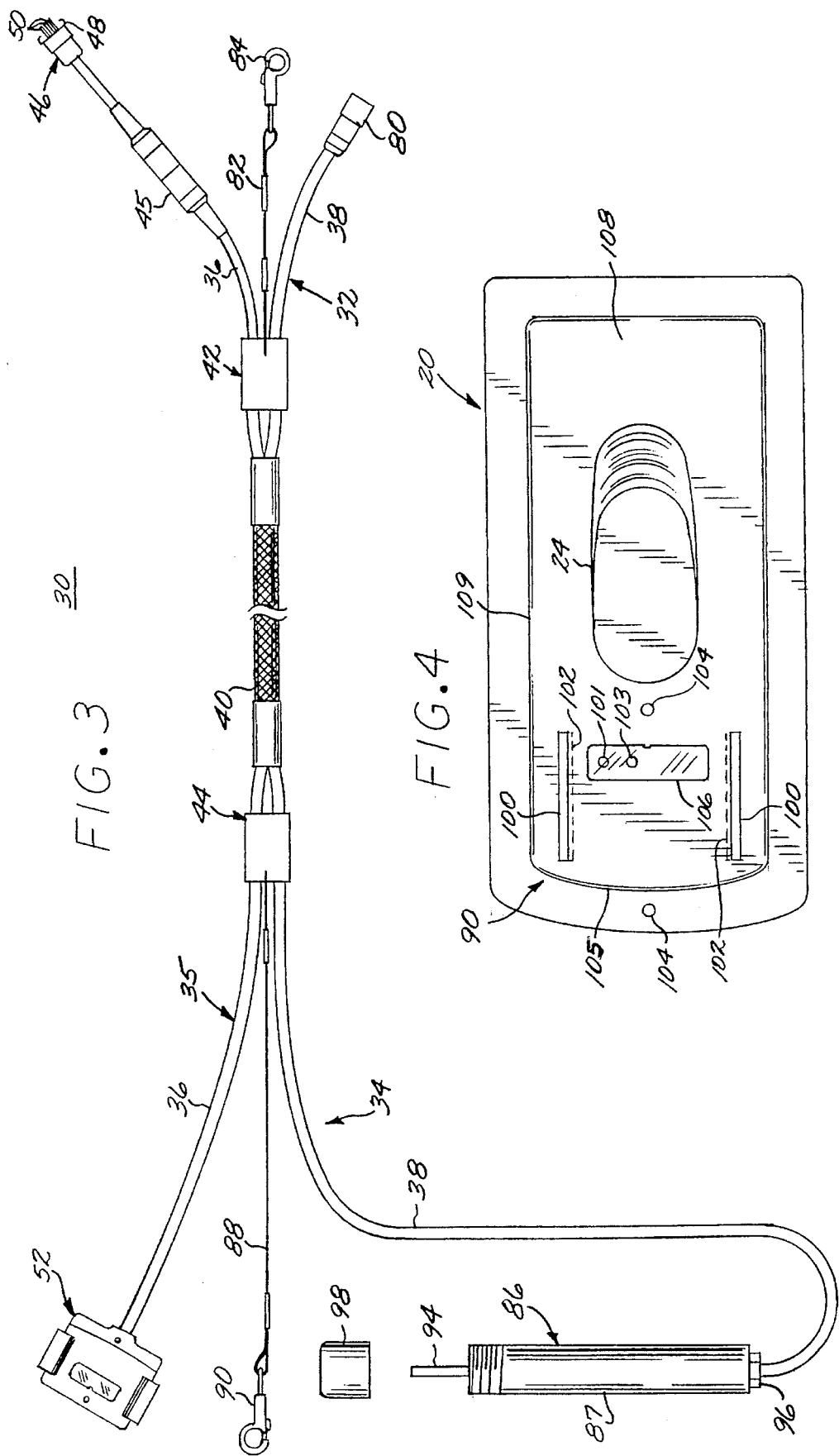

ELECTRICAL/OPTICAL INTERFACE COUPLER

BACKGROUND OF THE INVENTION

1. Field of the Invention

The invention is related to devices used to couple instruments together for data transmission therebetween and, more particularly to a device for coupling an instrument having an electrical interface and an instrument having an optical interface.

2. Description of the Prior Art

It is well known in the art that analytical instruments and the like are used to capture measurement data. Such data is represented by electrical signals which may easily be manipulated in desired formats. These electrical signals may be in either digital or analog form. Once this data is transformed into electrical signals, it is often desirable to transfer the electrical signals to cooperating instruments to trigger operations by those instruments or for data storage and data manipulation or the like. Such data may be transferred and received electrically by an electrical interface provided between the two instruments.

Some instruments are designed to communicate or otherwise transfer and receive data optically. It is well known in the art that electrical signals may be converted to optical signals and the data representative thereof transferred optically to cooperating instruments. These types of instruments generally communicate through optical interface ports.

Because instruments may have non-compatible communication interface ports, it becomes necessary to provide a communication link adapted for use between such non-compatible interfaces.

For example, such a dilemma has presented itself in the development of some portable gas monitoring systems. In this area of endeavor, federal, state, and local regulations have been implemented which require manufacturers or others handling hazardous materials to monitor potentially hazardous and/or explosive environments about their facilities. In particular, these regulations require periodic monitoring of potential release points such as valves, fittings or the like which pose a potentiality for leakage or emission of substances including toxic, hazardous and/or explosive material. Because some of these affected facilities include intricate piping systems having hundreds of potential release points, sampling of these points becomes quite time consuming and burdensome. As a result, portable monitoring systems have been developed which include a portable hazardous gas analyzer subsystem working in conjunction with a separate portable data collector/processor subsystem for storing data corresponding to concentration values of the hazardous constituents sensed by the gas analyzer at a release point. The data collector/processor subsystem may include a bar code reader to identify a potential release point and include a means of corresponding the identification data with sensed emissions data. A gas monitoring system of this nature is disclosed in U.S. Pat. No. 5,099,437 and is hereinafter incorporated by reference. The gas analyzer subsystem of this monitoring system has an electrical interface, such as a typical RS-232 connector, while the data collector/processor subsystem has an optical interface. Therefore, it becomes necessary to provide a coupling device to facilitate communication between the two instruments having these non-compatible interfaces.

In addition, since these instruments are utilized in potentially hazardous and/or explosive environments, the coupling device must be "intrinsically safe". National standards have been adapted in the United States for "intrinsically safe" equipment, as set forth in the National Electrical Code (NEC). For an instrument to be certified as intrinsically safe, it must be demonstrated that the equipment cannot produce a spark which could cause combustion or produce any other undesired effects in a potentially hazardous environment. An atmosphere having the presence of volatile gases, vapors or flammable liquids are examples of such a potentially hazardous environment. The electrical circuitry in these instruments must not be capable of producing a spark, even if failure of any of the electrical components in the circuitry occurs.

Hence, those skilled in the art have recognized the need to provide an intrinsically safe coupling device to facilitate communication between two instruments, wherein one such instrument has an optical interface and the other instrument has an electrical interface. Such a coupling device should be easily connectable, releasable and cost effective to produce. The present invention meets these needs and others.

SUMMARY OF THE INVENTION

The present invention is directed to a device for allowing communication between two instruments and specifically where one of such instruments has an electrical interface and the other such instrument has an optical interface. More particularly, the invention is embodied in a removable interface coupling, wherein the coupling itself converts electrical signals to optical signals and visa-versa.

The coupling device includes an electrical cable having first and second ends, one end attached to an electrical interface connector and the other end attached to an optical interface connector housing. The electrical interface connector is configured for releasable engagement with the instrument having the electrical interface. The optical interface connector housing includes a fastener configured for releasable engagement with the instrument having the optical interface. The fastener includes components which allow for secure engagement and accurate alignment of the connector housing with the optical interface for positive optical signal transmission therebetween. The optical interface connector housing of the coupler may receive electrical signals from the electrical signal interface and thereafter convert such electrical signal into an optical signal which subsequently is transmitted to the optical signal interface. Alternatively, or in combination with the aforementioned, the housing connector may receive optical signals from the optical interface and convert such optical signal to an electrical signal for receipt by the electrical interface.

In a more particular aspect of the invention, the foregoing coupling device is used to interconnect two subsystems of a portable gas detection system, one such subsystem having an electrical interface and the other subsystem having an optical interface. As such, the coupling is formed in combination with transportation tube.

Other features and advantages of the invention will become apparent from the following detailed description, taken in conjunction with the accompanying drawings, which illustrate by way of example the features of the invention.

BRIEF DESCRIPTION OF THE DRAWINGS

FIG. 3 is a broken top plan view, in enlarged scale, of the coupler shown in FIG. 1;

FIG. 4 is a bottom view, in enlarged scale, of an optical signal generating and receiving instrument included in the electrical/optical interface coupler shown in FIG. 1;

DETAILED DESCRIPTION OF THE PREFERRED EMBODIMENTS

Figure 1:
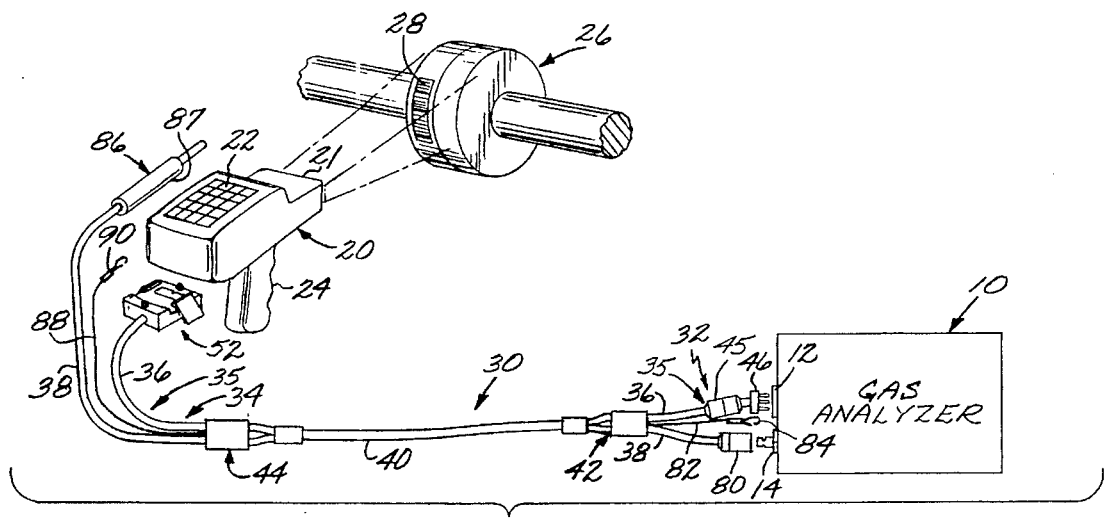
FIG. 1 is a perspective view of an electrical/optical interface coupler embodying the present invention.

As shown in the drawings for purposes of illustration, the invention is embodied in a removable coupling inter-connectable between two analytical instruments and more particularly with one such instrument having an optical communications interface and the other instrument having an electrical communications interface.

Analytical instruments are used to capture and manipulate measurement data. To add to the overall capability, it is desirable that such instruments be adapted for downloading and transferring of data to other instruments. For communication between two instruments to occur, a communications link must be provided, the link generally facilitated by respective communications interface ports on each instrument. However, communication between instruments having non-compatible communication interfaces creates a problem. For instance, some devices communicate through electrical interfaces while other instruments communicate through optical interfaces. In particular, some portable gas monitoring systems include a portable hazardous gas analyzer subsystem having an electrical interface working in communication with a portable data collector/processor subsystem having an optical interface. To provide communication between the two non-compatible interfaces, a conversion must be made.

A convenient inexpensive solution is to provide a coupling device including the interface conversion therein which will facilitate communication between the two gas monitoring subsystems. So that a coupling device of this nature may be utilized in potentially hazardous and/or explosive environments, the coupling should be certified as "intrinsically safe" thereby demonstrating that it cannot produce any undesired effects that could cause combustion in a potentially hazardous environment.

Referring to FIG. 1, a combination coupler of the preferred embodiment of the invention is shown for use with a portable hazardous emissions monitoring and detection system as described above. A potential emissions release point is depicted as a flanged fitting 26 connecting two lengths of a hazardous materials transportation pipe. The flanged fitting has been tagged with a bar code 28 for ease of identification.

The portable hazardous emissions detection system includes a gas analyzer, generally shown at 10, a portable data collector/processor, shown generally at 20, and the combination coupler of the invention, shown generally at 30. The portable data collector/processor has a sealed housing formed in its rear portion with a downwardly facing transparent optical transmission window 106 (FIG. 4) defining an optical interface. The gas analyzer is manufactured to be intrinsically safe and has an electrical receptacle 12, defining an electrical interface, and a gas sample inlet port 14. The gas analyzer receives a sample of air taken at the release point, analyzes such sample, and generates an electrical signal representative of a concentration of hazardous constituents present in the air sample. Typically, the electrical signal generated by the gas analyzer is an analog signal, but it is to be appreciated that such electrical signal may be digital in form.

The combination coupler 30 is releasably connectable between the aforementioned gas analyzer 10 and portable data collector/processor 20. The combination coupler, in general, includes a gas sample tube 38 integrally formed with an electrical/optical interface coupling 35. The interface coupling has an optical interface housing connector 52 for releasable connection to the optical interface of the portable data collector/processor 20 and an electrical interface connector or electrical plug, generally designated 46, connectable to the electrical receptacle 12 of the gas analyzer 10. The gas sample tube 38 includes a gas port connector 80 that is releasably connectable to the inlet sample port 14 of the gas analyzer. At the opposite end thereof, a sample wand 86 may be releasably attached to the body of the portable data collector/processor 20 using a hook and loop type velcro strip or the like.

Carried on a pistol grip handle 24, the portable data collector/processor 20 is generally box shaped and includes a forwardly facing bar code window 21 for transmission of optical signals to an internal bar code reader arranged to read a bar code at potential release points such as the bar code 28 shown disposed at the potential release point 26. The portable data collector includes an internal processor for processing data received from the gas analyzer 10 and further includes a memory in which to store such analyzer data and identification signals representative of indicia on such bar codes corresponding to emissions samples taken at the tagged release points. The portable data collector/processor also includes a manual input circuit for receiving control signals from an upwardly facing keypad 22 for manual data input which may supplement data pertaining to a particular release point.

It is a characteristic of commercially available collector/processors 20, such as those available on the market from Symbol Technologies, Inc., that the housing 21 and components thereof are intrinsically safe for use in hazardous gaseous atmospheres and the like. This feature is maintained so long as the housing is not penetrated or the integrity thereof otherwise violated. One of the objects of the present invention is to communicate data to and from such data processor without disturbing the integrity of its intrinsically safe character. To this end, advantage is taken of the optical interface provided by the optical interface window 106 of the data collector/processor 20 overlying an optical-to-electrical transducer, such as an optical detector 101 (FIG. 4) and an electrical-to-optical transducer such as an optical transmitter 103 (FIG. 4). The optical detector 101 may be a photo transistor or a photo diode, and the optical transmitter 103 may be a light emitting diode (LED) or an infrared emitter. Electronic circuitry is employed within the data collector/processor to receive data from the gas analyzer 10 via the optical detector.

As shown in FIG. 4, the underside of the portable data collector/processor housing is formed with a flat raised central surface 108 having a recessed border 90 about the periphery thereof to form, at the rear end thereof, a lateral projecting lip 105. Incorporated on the underside of such data collector/processor is a pair of laterally spaced apart, longitudinally extending, parallel retainer slots 100, each formed on their laterally inner sides with laterally outwardly opening grooves 102 to define upwardly facing retainer shoulders. A pair of small downwardly opening locator bores 104 are spaced longitudinally apart on the underside of such data collector on opposite sides of the window 106.

With particular reference to FIG. 3, the combination coupler 30 is hereafter described in detail. The combination coupler integrally combines the electrical/optical interface coupling 35 having an elongated electrical cable 36 with a gas sample tube 38. The combination coupler is elongated to form first and second ends, generally shown respectively at 32 and 34. An elongated tubular sheath 40 encases the central portion of the electrical cable 36 and gas sample tube 38 to gather the cable and tube along an intermediate length thereof. Respective first and second splitters 42 and 44 are disposed at either end of the sheath to transition the electrical cable and gas sample tube to their respective separated first and second ends 32 and 34. A first stainless steel tether cable 82 is attached to the first splitter 42 at one end and includes a first releasable clasp 84 attached to the opposite end thereof. Likewise, a second stainless steel tether cable 88 is attached to the second splitter 44 at one end and includes a second releasable clasp 90 attached to its opposite end thereof. The first clasp 84 may be attached to a hook (not shown) disposed on the gas analyzer 10 (FIG. 1) and the second clasp 90 attached to a hook (not shown) on the portable data collector/processor 20. When the clasps are attached, the respective tethers prevent the transfer of undue tension to the combination coupler assembly preventing damage to end connectors and/or to the integrity of the combination coupler itself. The electrical cable 36 consists of a plurality of electrically conductive wires surrounded by a protective insulation coating. The electrical/optical interface coupler 35, at the first end thereof, includes a fuse housing 45 that houses two 1/16 amp fuses therein. The fuse housing is separable for fuse replacement. At the free extremity of the electrical cable is an electrical plug, indicated generally at 46. The plug includes a plurality of electrical conductive pins 50 (shown here as three) connected to the respective aforementioned plurality of wires which are receivable in a receptacle 12 (not shown) of the gas analyzer 10. The plug 46 includes a twist-lock fitting 48 rotatable with respect to the plug which securely yet releasably engages the electrical interface 12. The second end of the electrical cable 36 is attached to the optical interface housing, the housing generally indicated at 52.

The first end of the gas sample tube 38 carries a gas sample port connector 80 including a snap locking mechanism to securely fit over and releasably engage the inlet gas sample port 14 of the gas analyzer 10. The second end 34 of the gas sample tube 38 is attached at the extremity thereof to one end of a cylindrical gas sample wand, generally designated 86, having an axial bore therethrough. The cylindrical wand is of a diameter which may be conveniently grasped in the hand of a workman taking gas samples in the field. The sample tube is attached to the bore of the wand at the bottom end thereof using a compression fitting 96 or the like. A removable stainless steel gas sample tube extension tip 94 is detachably connectable to the top end of the bore. The extension tip may be useful to detect emissions at potential release points in confined or restricted areas inaccessible by the wand. The tip may be removed and a wand cap 98 screwed over the tip of the wand to protect the gas sample tube and gas analyzer 10 from infiltration of extraneous particulates when the gas analyzer is not in use. A releasable fastener, such as a velcro hook-type strip 87 may be secured to the wand along the length thereof, allowing the workman to attach the wand conveniently to a respective velcro loop-type strip (not shown) on the side of the portable data collector/processor 20.

Since it is desirable to have flexibility in using the combination coupler 30 in potentially hazardous and/or explosive environments, the coupler is constructed to be "intrinsically safe". As mentioned above in the Background, a United States "intrinsically safe" rating applies to a classification of equipment which has been shown to meet the applicable standards as set forth in the National Electrical Code (NEC). For equipment to qualify as intrinsically safe, it must be constructed so that it will not produce a spark or any other undesired effects that could cause combustion in a potentially hazardous environment. The circuitry in such equipment must be selected to resist producing a spark, even if an electrical component contained in the circuitry should fail. Taken with this in mind, the combination coupler 30 and particularly the electrical/optical interface coupling 35 incorporates safety features and electronic design methodology to achieve an intrinsically safe designation. In addition to the selection of components forming the optical interface housing 52 (described hereafter) and the selection of particular electrical components housed therein, the electrical cable 36 includes features facilitating an intrinsically safe device. For instance, as described above, the electrical cable incorporates a plurality of independently insulated conductive wires all encased in a protective insulation coating and at the first end thereof includes a fuse housing 45 which houses two 1/16 amp fuses.

In another embodiment, the electrical/optical interface coupler 35 is constructed without the gas sample tube 38 in combination therewith. In referring particularly to FIG. 2, the optical interface housing 52, included in both this and the combination coupler embodiments, can be further described hereinafter. The housing 52 is rectangular shaped and formed on its bottom side with a raised limit lip 55 (FIG. 5) at the rear end thereof and a flush mounted housing window 54 disposed centrally thereon. Such window 54 is transparent and is disposed in close spaced relationship over an electrical-to-optical transducer or optical transmitter 56, such as a light emitting diode (LED) or an infrared emitter. Spaced laterally apart therefrom is an optical-to-electrical transducer or optical detector 57 such as a photo diode or photo transmitter. The optical transmitter 56 and optical detector 57 respectively transmit and receive optical signals. The optical window is formed of a transparent shock resistant material, such as high impact hard plastic, to protect the optical transmitter and detector from incidental impact.

A releasable connector device is provided to securely engage the optical interface housing 52 to the optical interface windows 106 of the portable data collector/processor 20. Such connector is in the form of a pair of pivotal fastener plates, generally indicated at 60, positioned in a parallel relationship on either side of the optical interface housing 52 for selective engagement in the fastener slots 100 (FIG. 4) on the underside of the data collector/processor 20. In addition, a pair of small diameter locator pins 58 protrude from the top surface of the housing 52 for selective engagement with the locator bores 104 of the data collector/ processor (FIG. 4).

Figure 5:
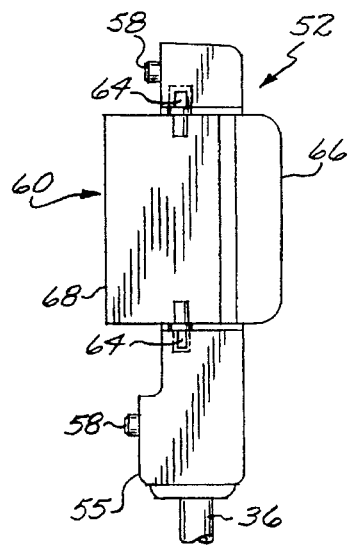
FIG. 5 is a side view, in enlarged scale, of an optical interface connector housing included in the electrical/optical interface coupler shown in FIG. 1.
Figure 6:
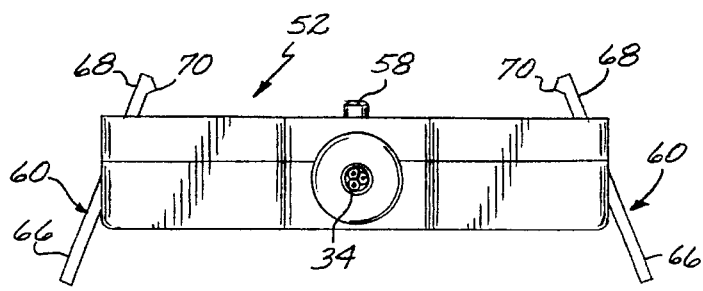
FIG. 6 is a sectional view taken along the line 6—6 of FIG. 2.

Referring to FIG. 5, the fastener plates 60 are elongated and are rotatably attached along their medial portions to the optical interface housing 52. The fasteners 60 are formed at their respective upper edges 68 to be slidably received in the respective data collector/processor slots 100 and are configured with respective interned hooks 70 for complemental receipt in the respective slots to be engaged in the respective grooves 102 (FIG. 4). The lower extremities of such plates 60 form respective hand pads 66. With continued reference to FIG. 6, the connector includes respective biasing springs urging the respective pads 60 rotatably about their respective horizontal pivot axis to bias the respective upper hook ends thereof inwardly toward one another.

Figure 7:
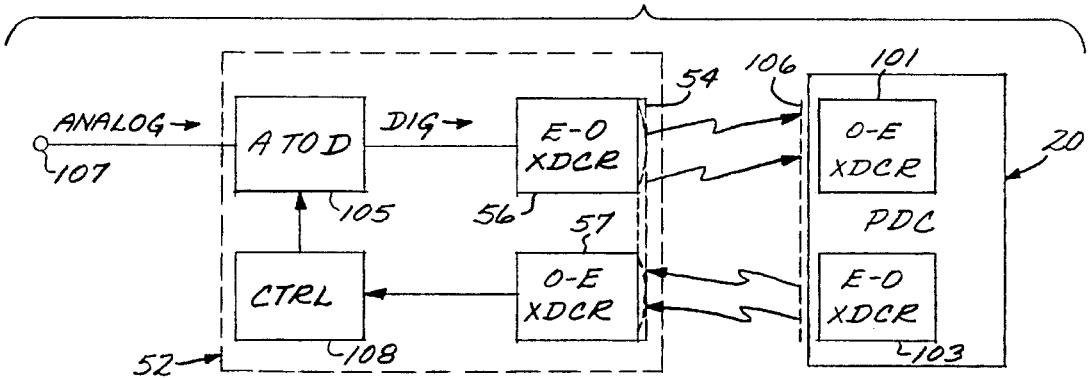
FIG. 7 is a block diagram of one embodiment depicting operation of the electrical/optical interface coupler shown in FIG. 1.

Referring to FIG. 7, the optical interface housing 52, in general, houses an analog-to-digital (A-D) converter 105, the electrical-to-optical transducer or photo transmitter 56 (FIG. 2), the optical-to-electrical transducer or photo detector 57 (FIG. 2), and a controller 108. An analog input lead 107 is in circuit with the A-to-D converter 105, the analog lead receiving analog signals from the gas analyzer. When desired to receive data from the gas analyzer, the portable data collector (PDC) 20 transmits an optical prompt signal from the photo transmitter 103 (FIG. 4) to prompt the coupler in optical interface housing 52 to transmit such gas analyzer data. The PDC optical prompt signal is transmitted from the PDC to the photo transmitter 103 (FIG. 4) through the respective transparent optical transmitter windows 106 and 54. The prompt signal is received by the optical-to-electrical (O-E) transducer or housing photo detector 57 (FIG. 2) which sends an electrical signal to the controller 108 to control the A-D converter to convert and transmit the analog data from the analyzer. The A-D converter converts the analog signal to a digital signal which is directed through a lead to the electrical-to-optical (E-O) transducer 56. The E-O transducer is responsive to the digital signal and transmits an optical signal through the respective optical transmission windows 54 and 106 to the PDC photo detector 101 (FIG. 4).

Figure 8:
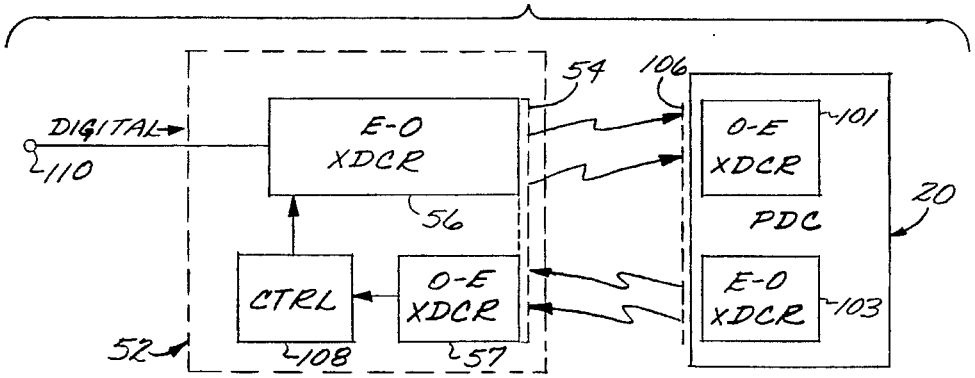
FIG. 8 is a block diagram of another embodiment depicting operation of the electrical/optical interface coupler shown in FIG. 1.

In another embodiment, shown in FIG. 8, the optical interface housing 52 is configured to receive a digital signal representative of gas sample data from the gas analyzer. As such, the interface housing 52 houses the electrical-to-optical (E-O) or photo transmitter 56 (FIG. 2), the optical-to-electrical (O-E) transducer or photo detector 57 (FIG. 2), and the controller 104. A digital input lead 106 is in circuit with the electrical-to-optical (E-O) transducer, the lead receiving digital signals from the gas analyzer. When the portable data collector/processor (PDC) 20 is ready to receive data from the gas analyzer, an optical prompt signal is transmitted from the photo transmitter 103 (FIG. 4) to prompt the coupler and interface housing 52 to transmit such digital gas analyzer data. The PDC optical prompt signal is transmitted from the PDC photo transmitter 103 through the respective optical transmission windows 106 and 54 and is received by the optical-to-electrical transducer or housing photo detector 57 (FIG. 2) which sends an electrical signal to the controller 108 to control the electrical-to-optical (E-O) transducer or photo transmitter 56 (FIG. 2) to transmit the digital data. The E-O transducer transmits an optical signal through the respective optical transmission windows 54 and 106 to the PDC photo detector 101 (FIG. 4).

In yet another embodiment of the invention, the optical interface housing 52 may include electronic components which are configured to transmit data from the portable data collector/processor 20 to the analyzer 10. As mentioned above, the optical interface housing is configured to receive optical prompt signals from the portable data collector/ processor. In an extension of this feature, these optical signals may carry collector/processor data for receipt by the gas analyzer. Using appropriate electronic circuitry, the signal may be connected to digital electronic signals communicated along the electrical/optical coupler to the electrical interface of the analyzer. If desired, the digital signal may be converted to an analog signal using a conventional digital-to-analog (D-A) converter well known in the art.

Figure 9:
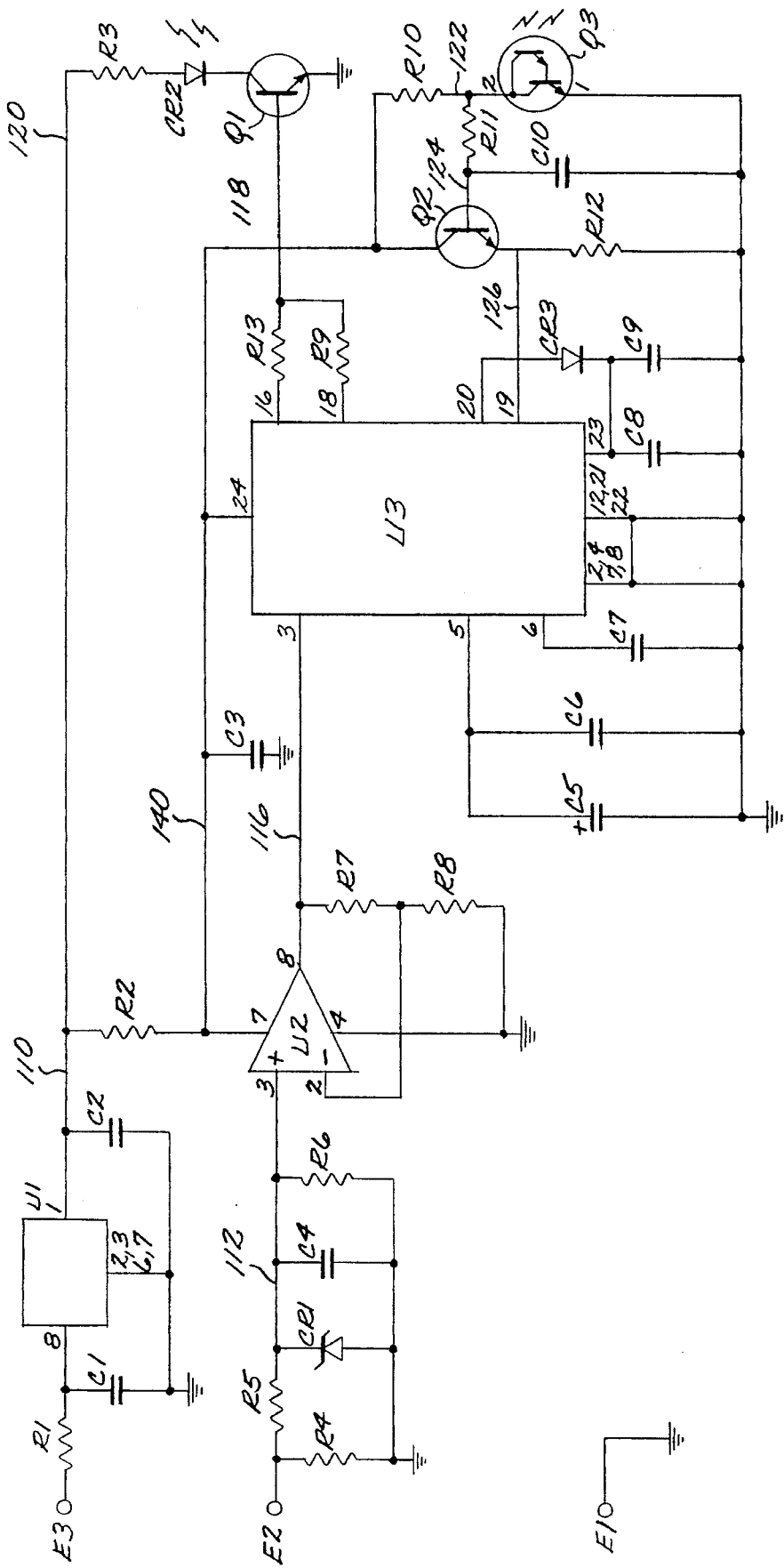
FIG. 9 is a schematic diagram of the electrical circuit included in the coupler embodiment shown in FIG. 7.

Referring particularly to FIG. 9, a schematic diagram of the electrical circuitry included in the optical interface housing 52 (FIG. 2) of the preferred embodiment is shown. The electrical components housed in the interface housing 52 receive electrical power from the gas analyzer 10 (FIG. 1) across schematic leads E1 (ground) and E3 (power). A voltage regulator U1 is located on signal line 110 and may be of the type made available from Motorola (part no. MC78L05ACD). The voltage of the power supplied may vary in amplitude without harm to the electrical components, because the voltage regulator U1 takes the input voltage and modifies its amplitude, outputting a near-constant predetermined voltage.

As described above, the gas analyzer 10, in the preferred embodiment, collects gas sample data and records that data in analog signal form. The analog signal is output by the gas analyzer for receipt by the optical interface housing schematically at signal input E2. A zener diode CR1 of the type, also made available from Motorola (Part. No. B7V55C8V2), is configured in parallel with a capacitor C4. The capacitor and the cathode of zener diode CR1 are connected to a common signal line 112 from input E2. Connected to common signal line 112 is the input to an operational amplifier U2. The operational amplifier may be of the type provided by Maxim (part no. MAX480CSA). A pair of 10,000 Ohm resistors, R7 and R8, are connected to common signal line 114. The output of the operational amplifier and the input of a twelve-bit analog-to-digital converter U3 are both connected to a common signal line 116. An appropriate analog-to-digital converter, such as that provided by Maxim (part no. MAX190BCWG) may be utilized. The output of the analog-to-digital converter U3 and the active base region of a transistor Q1 are both connected to a common signal line 118.

Figure 2:
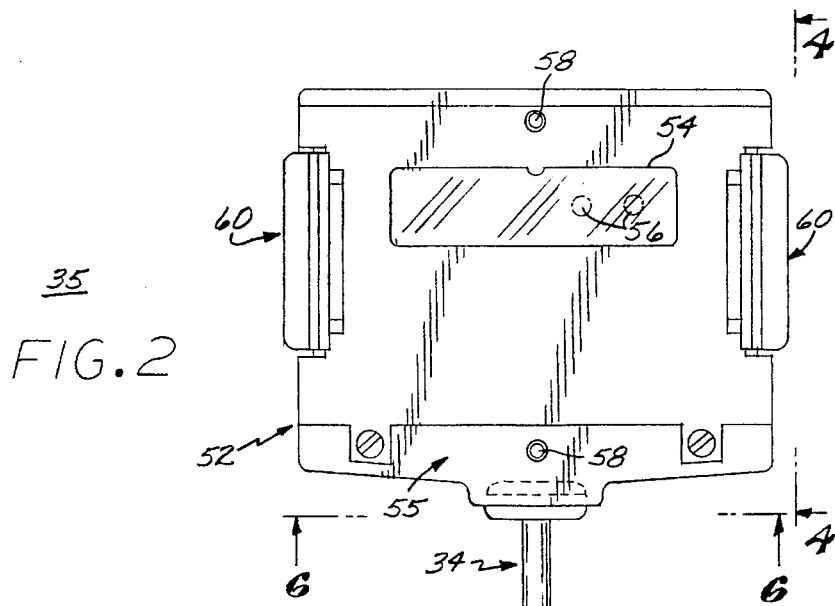
FIG. 2 is a broken bottom view, in enlarged scale, of a second embodiment of the electrical/optical interface coupler embodying the present invention.

The aforementioned components are of the type well known in the art and thus are not described in further detail. An LED (light emitting diode) CR2 of the type, for instance, made available by Motorola (part no. MLED71) is utilized and more specifically defines the optical transmitter 56 (FIG. 2) of the housing interface. The LED is connected to the common signal line 120 and is configured such that its cathode is tied to the collector region of the transistor Q1. A photo detector Q3, likewise of the type made available by Motorola (part no. MRD 711), more specifically defines the optical detector 57 (FIG. 2). The photo detector Q3 is connected to common signal line 122 and consists of a pair of transistors, one of such transistor having no base lead. The transistor having no base lead is a photo transistor which receives an optical signal by means of illumination on its exposed base region to convert optical signals to corresponding electrical signals. The collector regions of both of the photo detector transistors and the base region of a transistor Q2 are connected to common signal line 124. The emitter region of transistor Q2 and the anode of a signal diode CR3 of the type, for instance, provided by Rohm (part no. RLS4149) are connected to common signal line 126. The cathode of the signal diode CR3 and a pair of capacitors C8 and C9 configured in parallel, are connected to a common signal line 128. Also connected to the common signal line 128 is the clock of the analog-to-digital converter U3.

The other electrical symbols and schematically illustrated components in FIG. 9 are listed as follows:

| Resistors: | |
|---|---|
| R1, R2 | = 10 ohm |
| R3 | = 330 ohm |
| R4 | = 3.0K ohm |
| R5 | = 6.81K ohm |
| R6 | = 9.09K ohm |
| R7, 8, 9, 11, 13 | = 10K ohm |
| R10 | = 1K ohm |
| R12 | = 4.7K ohm |
| Capacitors: | |
| C1, 2, 6, 7 | = 0.1 UF |
| C3 | = 22 UF |
| C4 | = 1. UF |
| C5 | = 4.7 UF |
| C8, 10 | = 0.022 UF |
| C9 | = 0.0022 UF |

Analog Ground
Digital Ground

To receive data from the gas analyzer, the portable data collector/processor transmits a one-bit signal optically from its optical transmitter 103 to be received by the photo detector Q3 or optical detector 57 (FIG. 2) of the optical interface housing. The one-bit signal is utilized to prompt the A-D converter to convert the analog signal provided by the gas analyzer into a corresponding digital signal and then output that digital signal, which begins the data transmission process. The one-bit prompt signal is directed to the active, exposed photo transistor base region of the photo detector Q3. This illumination on the active base region induces a base current in the first photo transistor of the photo detector Q3 to actuate the photo transistor. When the photo transistor of the detector Q3 is activated, a current flow is induced in its emitter region. Such emitter is tied to the base region of a second transistor of the photo detector Q3. The current flow to the active base region of the second transistor activates the second transistor. With both transistors activated, a voltage potential is induced, the induced voltage creating current which flows to the active base region of transistor Q2, in turn activating transistor Q2. A current is then induced in the emitter region of transistor Q2 which flows through signal diode CR3 resetting the clock of the analog-to-digital converter U3. The housing electronics are now in condition to convert and transmit the analog signal being received from the gas analyzer. The analog signal received is first modified by the zener diode CR1 and the capacitor C4. The zener diode is employed to prevent excessive signal amplitudes from reaching and damaging the remaining circuitry of the A-D coupler. The zener diode acts to regulate any input signals that exceed normal input levels, thereby outputting to the remaining circuitry a voltage that will not damage any of the components. It also is used to clamp high voltage electro-static discharge (ESD) that may developing field use. A zener is preferred because it will clamp both positive and negative ESD surges. The capacitor C4, connected in parallel with the zener diode, has the effect of filtering noise distorting the analog signal, thereby providing a free signal to the input of the operational amplifier U2. The operational amplifier is configured to act as a non-inverting amplifier of the analog signal it receives. A pair of 10,000 Ohm resistors, R7 and R8, are connected to signal line 114 such that the amplitude of the signal output by the operational amplifier U2 is twice that of the input.

This output signal is then input to the twelve-bit analog-to-digital converter U3. The analog-to-digital converter receives the analog signal and transforms it into a corresponding digital signal. After the clock is reset, the analog-to-digital converter outputs the digital signal which is received in the active base region of transistor Q1. The transistor Q1 has a current injected into its base and is thereby activated. This allows for current to flow through the LED CR2 and into the collector region of the transistor Q1. When current flows through the LED, CR2 an optical signal corresponding to gas analyzer data is transmitted for receipt by the optical detector 101 (FIG. 4) of the data collector/processor. The data collector/processor receives this optical signal, converts such optical signal to an electrical signal corresponding to the gas analyzer data and such data is thereafter stored by the data collector/processor.

Referring to FIG. 1, in operation, the portable gas monitoring system is employed at a field site where gas monitoring is desired. The gas analyzer 10 and portable data collector/processor 20 are interconnected using the combination coupler 30 of the preferred embodiment. The workman attaches the first end 32 of the coupler to the gas analyzer. As such, the gas sample tube port connector 80 is coupled to the analyzer inlet sample port 14 and the plug 46 of the electrical cable 36 is coupled to the analyzer receptacle 12. The clasp 84 of the first tether 82 is then hooked to the analyzer. The workman may now connect the second end 34 of the combination coupler to the portable data collector/processor 20. As such, the workman attaches the velcro strip 87 of the wand 86 to the side of the collector/processor 20 and hooks the clasp 90 of the second tether 88 to the collector/processor. To connect the optical interface housing 52 to the collector/processor, the workman grasps the lower hand pads 66 of the respective housing fasteners 60 (FIG. 6), for instance, between his or her thumb and forefinger to draw the lower ends thereof together against the bias of the biasing spring thus spreading the confronting upper edges 68 away from each other. The fasteners are separated far enough apart to align the upper edges 68 thereof with the elongated fastener slots 100 of the portable data collector/processor and thereafter urged into the respective slots 100 (FIG. 4). The alignment pins 58 of the housing are received in the respective alignment holes 104 of the collector/processor and the housing lip 55 is aligned with the ridge 109 of the collector/processor to thus align the respective interned hooks 70 with the respective grooves 102. The workman may then release the fasteners so that the fastener hooks 70 are biased into the respective grooves 102. As such, the housing is securely connected to the collector/processor and the housing window 54 and data collector window 106 are in confronting alignment wherein optical transmitter 56 and optical detector 57 of the optical interface housing 52 are properly and accurately aligned with the respective optical detector 102 and optical transmitter 103 of the data collector/processor 20.

With the gas analyzer 10 and data collector/processor 20 properly interconnected with the combination coupler 30 (FIG. 1), the workman may activate the data collector/processor bar code reader subsystem and identify a bar code at the selected release point 26, the point identified being stored therein. Thereafter, the workman may take a sample of air at the sample point using the sample wand 86, the gas sample being transported to the analyzer 10 through the gas sample tube 38. Analysis of the sample is performed by the gas analyzer and an analog signal, for instance, representative of the concentration of gas sampled is generated and transmitted along the electric cable 36 to the optical interface housing 52. With Reference to FIG. 7, the portable data collector/processor transmits an optical prompt signal to the interface housing and the analog signal is thereafter converted by the A-D converter 106, to a digital signal and the digital signal is then sent to the photo transmitter 56 and an optical signal is transmitted. The optical signal is transmitted through the respective transmission windows 54 and 106 and the data collector/processor photo detector 101 receives the signal. The gas analyzer data is sent to the data collector interval memory for storage or to the internal processor for processing. In this fashion, a multitude of release points can be sampled and the sample data representative thereof being stored and processed by the collector/processor.

At the end of a sampling route, the combination coupler can be disconnected from the portable data collector/processor and stowed for subsequent use. Thereafter, the collector/processor may be coupled to a host computer via the optical interface port to download the collected data for further processing and data storage.

As can be appreciated from the foregoing, the intrinsically safe electrical/optical interface coupler of the invention provides a reliable inexpensive means to inter-connect and provide communication between an instrument having an optical interface and an instrument having an electrical interface. The coupling has an optical interface housing including electronics therein which appropriately convert and analog or digital signal to an optical signal for receipt by the instrument having the optical interface. The housing also includes electronics which may receive optical signals and convert such signals to electrical signals so that the coupler may perform both optical-to-electrical and electrical-to-optical communication simultaneously. The optical interface housing has an easy to operate fastener which securely attaches the housing to the optical interface to provide accurate alignment of the optics contained therein with the optics of the instrument having the optical interface.

It will be apparent from the foregoing that, while particular forms of the invention have been illustrated and described, various modifications can be made without departing from the spirit and scope of the invention. Accordingly, it is not intended that the invention be limited, except as by the following claims.

What is claimed is:

1. A removable coupler inter-connectable between an electrical interface of an analog signal generating device and an optical interface of an optical signal receiving device and comprising:

an elongated flexible cable having electrical and optical ends and including an electrical conductor housed therein and leading from said electrical end;

an electrical connector attached to said cable at said electrical end for being releasably connected to said analog signal generating device;

an optical interface housing attached to said cable at said optical end, said housing including a releasable connector for releasably connecting said housing to said optical signal receiving device, and a circuit for receiving an analog signal generated from said analog signal generating device and converting said analog signal to a digital signal; and an optical emitter mounted in said optical interface housing and electrically connected to said circuit and responsive to said digital signal from said circuit to generate a corresponding optical signal for transmission to said optical signal receiving device.

2. A removable coupler as set forth in claim 1 wherein:
   said lead includes an intermediately disposed separable fuse housing for carrying a fuse therein.

3. A removable coupler as set forth in claim 1 wherein:
   said connector of said optical interface housing includes at least one releasable fastener to securely engage said optical signal receiving device.

4. A removable coupler as set forth in claim 3 wherein:
   said optical signal receiving device includes a housing formed with at least one elongated slot for engagement to at least one respective said fastener.

5. A removable coupler as set forth in claim 1 wherein:
   said optical interface housing includes a transparent optical signal transmission window and said optical signal receiving device includes a transparent optical signal receiving window.

6. A removable coupler as set forth in claim 5 wherein:
   said optical signal receiving device includes a housing formed with at least one alignment hole, said optical interface connector includes a confronting surface including at least one alignment pin for respective receipt in said hole, said hole and said alignment pin operable to align said optical signal transmission window with said optical signal receiving window.

7. A removable coupler as set forth in claim 1 wherein:
   said optical interface housing includes an optical detector for receiving optical prompt signals from said optical signal receiving device to prompt said optical transmitter to transmit said digital signal.

8. Electrical/optical converter cable apparatus for removably coupling between an electrical outlet of an electrical analyzer device generating an electrical signal and a portable data collector housed in an intrinsically safe housing formed with an optical interface having a predetermined configuration and including an optical sensor behind an optical window, said apparatus comprising:

an elongated, intrinsically safe flexible cable having first and second ends and including an electrical conductor housed therein and leading from said first end;

an electrical connector attached to said first end for connection to said electrical outlet;

a converter device carried from said second end and including a housing formed with an optical connector having an optically transparent window configured to complementarily mate with said optical interface and including an optical emitter electrically connected to said electrical connector and positioned to, when said converter device is mated with said optical interface, align in signal transmitting relation with said optical sensor; and a releasable mechanical coupler for releasably coupling said converter device to said data collector with said transparent window complementarily mated with said optical interface whereby said electrical connector may be connected with said electrical outlet and said converter device coupled to said data collector without invading said intrinsically safe housing to thereby establish an intrinsically safe coupling between said analyzer device and data collector to provide for communication therebetween.

9. Electrical/optical converter cable apparatus as set forth in claim 8 for use with said data collector device that is portable and wherein:

said cable is elongated and flexible to allow for said data collector, while said electrical connector is connected to said outlet and said converter device coupled to said data collector, to be manipulated about relative to said first end.

10. Electrical/optical converter cable apparatus as set forth in claim 8 wherein:

said data collector device is portable and includes a bar code scanner to identify identification codes from different locations and a memory for storing said identification codes;

said cable includes a portable sensor for sensing predetermined conditions at the respective said locations and a communication line leading from said sensor to said analyzer device, said sensor being responsive to the sensing of said predetermined conditions at said locations to conduct said conditions to said analyzer device; and said analyzer device is responsive to said conditions received from said communication line to generate a corresponding electrical signal transmitted along said conductor to said optical emitter.

11. Electrical/optical converter cable as set forth in claim 8 wherein:

said converter device includes an analog to digital converter electrically connected to said electrical conductor and optical emitter and responsive to an analog signal from said electrical conductor to generate a corresponding digital signal for transmission to said optical emitter.

12. A removable coupler inter-connectable between an electrical interface of an electrical signal transmitting device and an optical interface of an optical signal receiving and transmitting device including a first optical emitter and receiver, said apparatus comprising:

an elongated flexible cable having electrical and optical ends and including an electrical conductor housed therein and electrically connected to said electrical and optical ends;

an electrical connector attached to said cable at said electrical end for releasable connection to said electrical signal transmitting device for transmission of electrical signals generated by said electrical transmitting device along said conductor;

an optical interface housing attached to said cable at said optical end, said housing including a releasable connector for releasably connecting said housing to said optical signal receiving and transmitting device;

a second optical emitter mounted in said optical interface housing and disposed at a predetermined position therein to, when said optical interface housing is connected to said optical signal receiving and transmitting device, align with said first optical receiver;

a second optical receiver mounted in said optical interface housing and disposed at a predetermined position therein to, when said optical interface housing is connected to said optical signal receiving and transmitting device, align with said first optical emitter for receipt of an optical signal from said first optical emitter to generate a corresponding electrical prompt signal; and an electrical circuit electrically connected to said second optical receiver, said second optical emitter, and to said conductor and responsive to said electrical prompt signal to transmit said electrical signals generated by said electrical signal generating device to said second optical emitter.

13. The coupler of claim 12 wherein:

said cable includes an intermedially disposed separable fuse housing for carrying a fuse therein.

14. The coupler of claim 12 wherein:

said connector of said optical interface housing includes at least one releasable fastener to securely connect said optical interface housing with said optical signal receiving and transmitting device.

15. The coupler of claim 12 wherein:

said optical interface housing includes an optically transparent signal transmission window and said optical signal receiving and transmitting device includes an optically transparent signal receiving window.

16. The coupler of claim 12 wherein:

said electrical signal transmitting device includes a signal generator for generating analog signals;

said circuit includes an analog to digital converter responsive to said analog signals to generate corresponding digital signals for transmission to said second optical emitter; and said second optical emitter is responsive to said digital signals to generate corresponding optical signals for receipt by said first optical receiver.

17. The coupler of claim 16 wherein:

said electrical signal generating device includes a portable emissions sensor to sense the concentration of a gaseous emission and generate a corresponding analog sense signal representative thereof; and said optical signal receiving and transmitting device includes a portable data collector including a memory tier receipt and storage of said optical signals.

18. A removable coupler and sensor assembly inter-connectable between an electrical interface and a sensor interface of an electrical signal transmitting device and an optical interface of an optical signal receiving device including an optical receiver, said apparatus comprising:

an elongated flexible cable having electrical and optical ends and including an electrical conductor housed therein and electrically connected to said electrical end;

an elongated sensor conduit connected to said cable and including a first end for releasable connection to said sensor interface and a free second end including a sensor for sensing a predetermined condition adjacent said sensor and for transmitting said condition through said conduit to said sensor interface of said electrical signal transmitting device;

an electrical connector attached to said cable at said electrical end for releasable connection to said electrical interface of said electrical signal transmitting device;

an optical interface housing attached to said cable at said optical end, said housing including a releasable connector for releasably connecting said housing to said optical interface; and an optical emitter mounted in said optical interface housing, electrically connected to said electrical conductor and disposed at a predetermined position therein to, when said optical interface housing is connected to said optical signal receiving device, align with said optical receiver, said emitter being responsive to electrical signals conducted along said electrical conductor to generate corresponding optical signals for transmission to said optical receiver.

19. The coupler of claim 18 wherein:

said cable includes a medially disposed separable fuse housing for carrying a fuse therein.

20. The coupler of claim 18 wherein:

said connector of said optical interface housing includes at least one releasable fastener to securely connect said optical interface housing with said optical signal receiving and transmitting device.

21. The coupler of claim 18 wherein:

said optical interface housing includes an optically transparent signal transmission window and said optical signal receiving device includes an optically transparent signal receiving window.

22. The coupler of claim 18 wherein:

said electrical signal transmitting device includes a signal generator for generating analog signals and further including:
- a converter circuit mounted in said optical interface housing and electrically connected to said conductor and responsive to said analog signals to generate a corresponding digital signal for transmission to said optical emitter and wherein:
- said optical emitter is responsive to said digital signal to generate a corresponding optical signal for receipt by said optical receiver.

23. The coupler of claim 22 wherein:

said converter circuit includes an analog to digital converter responsive to said analog signal to generate said corresponding digital signal for transmission to said optical emitter.

24. The coupler of claim 18 wherein:

said electrical signal transmitting device includes a portable emissions sensor for sensing a gaseous emission and responsive to a condition thereof to generate a corresponding sense signal representative thereof; and said optical signal receiving device includes a portable data collector including a memory for receipt and storage of said optical signals.

* * * * *

UNITED STATES PATENT AND TRADEMARK OFFICE
CERTIFICATE OF CORRECTION

PATENT NO. : 5,578,834
DATED : November 26, 1996
INVENTOR(S) : Rex Trobridge

It is certified that error appears in the above-identified patent and that said Letters Patent is hereby corrected as shown below:

Column 2, line 57, after "with" insert --a gas sample--;

Column 11, line 28, delete "and" and insert --an--;

Column 14, line 31, delete "tier" and insert --for--.

Signed and Sealed this

Twenty-first Day of January, 1997

Attest:

BRUCE LEHMAN

*Attesting Officer*      *Commissioner of Patents and Trademarks*